United States Patent [19]
Kato et al.

[11] Patent Number: 5,084,279
[45] Date of Patent: Jan. 28, 1992

[54] BIOACTIVATED PEARL

[76] Inventors: Masatoshi Kato, 38 Kumano-cho; Masuhiro Kato, 19 Minase-cho, both of, Seto-shi, 489 Aichi, Japan

[21] Appl. No.: 340,853

[22] Filed: Apr. 20, 1989

[51] Int. Cl.$^5$ .......................... A61K 7/16; A01N 63/2
[52] U.S. Cl. ........................................ 424/547; 424/49
[58] Field of Search ........................ 424/95, 49, 547; 514/866

[56] References Cited

U.S. PATENT DOCUMENTS 3,944,661   3/1976   Colodney et al. ................. 424/49
4,783,975  11/1988   Komatsu et al. .................... 63/32

FOREIGN PATENT DOCUMENTS 982946   2/1976   Canada ............................... 424/49

OTHER PUBLICATIONS

Folk Medicine; The Art and the Science, Ed: R. P. Steiner (1986) American Chemical Society, p. 48.

Primary Examiner—Allen J. Robinson
Assistant Examiner—Gary E. Hollinden
Attorney, Agent, or Firm—Cooper & Dunham

[57] ABSTRACT

A bioactive material is obtained by heating pearl. A calcium component and conchiolin, which is contained in pearl, are activated by heating. Said bioactive material is useful as a plant growth agent, an animal growth agent, a fish growth agent, a medicine, a preservative, and the like.

4 Claims, No Drawings

BIOACTIVATED PEARL

FIELD OF THE INVENTION

The instant invention relates to a bioactive material obtained by heating pearl.

More particularly, the instant invention relates to a bioactive material obtained by heating pearl, which is useful as a plant growth agent, an animal growth agent, a fish growth agent, a medicine, a preservative, and the like.

DESCRIPTION OF THE PRIOR ART

Since olden times, pearl has been used as a panacea in China, Europe, and other areas. It seems that the effective components of pearl are a calcium component and conchiolins, which is a kind of protein contained in pearl. nevertheless, the effectiveness of pearl as a medicine has not so remarkable.

SUMMARY OF THE INVENTION

Accordingly, an object of the instant invention is to increase the effectiveness of pearl as a bioactive material. A further object of the instant invention is to provide a bioactive material useful as a plant growth agent, an animal growth agent, a fish growth agent, a medicine, preservative, and the like. Briefly, said objects of the instant invention can be attained by heating pearl.

DETAILED DESCRIPTION

A bioactive material of the instant invention is obtained by heating pearl, desirably at a temperature in a range between about 200° to about 1,600° C., more desirably about 400 to about 1,500° C. Before pearl is heated, it is desirable that said pearl be shattered to powder and therefore, said bioactive material be provided in a powder form. It has been clarified that pearl heated at a temperature in a range between 700° to 800° C. is effective for animals, and pearl heated at a temperature in the range between 900° to 1,100° C. is effective for plants. Many kinds of chemical agents such as calcium sulfate, calcium carbonate, calcium phosphate may be mixed with said bioactive material and further, shell powder, bone powder, coral powder, carapace powder of Crustacea, limestone powder and the like ma also be mixed with said bioactive material. Pottery, earthenware, glass, ceramics and the like which contain said bioactive material are also effective as bioactive materials. Further, pottery, earthenware, and the like, on which glaze containing said bioactive material are put, are also effective as bioactive materials. Still further, pottery, earthenware, and the like containing said bioactive material, on which glaze containing said bioactive material are put are also effective as bioactive materials. When said bioactive material is used, said bioactive material may be directly administered to animals, fish and the like as an oral medicine or applied to an affected part of an animal, fish and the like as an ointment, and said bioactive material may be mixed with soil for plants.

Further, water in which said bioactive material, said pottery, earthenware, glass, ceramics, and the like are dipped, is also effective as a bioactive material. Said water may be used as an oral medicine, an ointment, an injected medicine, and the like for animals, fish and the like and said water may also be used for the breeding of fish. Said water may be also used for water culture. In said use, said bioactive material may be effective as a treatment medicine or a preventive medicine against many kinds of disease such as hyperpiesia, diabetes, cancer, allergic diseases, skin diseases, women's diseases, and the like, or a hygienic medicine, or a growth agent for animals, fish, and plants. Further, said bioactive material may be effective as a preservative for meat, fish, vegetables, water, and the like, or a fungicide for wood, plastic, food, textiles, and the like.

EXAMPLE 1

[Preparation of a bioactive material]

Bioactive material was prepared by heating pearl powder at a temperature between 700° to 800° C. for 6 hours.

EXAMPLE 2

[Manufacture of pottery balls]

About 15% by weight of the bioactive material of Example 1 was mixed into potter's clay and said potter's clay was molded into balls having an average diameter of about 20 mm. Said balls were heated at a temperature between 700° to 750° C. for 5 hours. Thus, pottery balls having bioactivity wer manufactured.

EXAMPLE 3

[Manufacture of glazed pottery balls]

A glaze containing 80% by weight of said bioactive material of Example 1 for a solid of said glaze was put on said pottery balls of Example 2 and said pottery balls were heated at a temperature between 1,300° to 1,350° C. for 30 hours. Thus, glazed pottery balls having bioactivity were manufactured.

EXAMPLE 4

[Treatment of hyperpiesia]

The bioactive material of Example 1 was orally administered to a hypertensive patient (male, 47 years old, highest blood pressure about 210, lowest blood pressure about 130) in a dosage of 0.5g per day. After said administration for six months, said highest blood pressure and said lowest blood pressure of said hypertensive patient dropped to about 130 and about 85 respectively and the blood pressure of said hypertensive patient has maintained a normal rang after said administration ceased.

EXAMPLE 5

[Treatment of angina pectoris]

The bioactive material of Example 1 was orally administered to a patient (male, 60 years old) suffering from angina pectoris, in a dosage of 0.5g twice per day and a further 600cc of water in which said pottery balls of Example 2 were dipped for 4 hours (5grs of pottery balls/1 l water) was orally administered per day. After said administration of said bioactive material and said water for one month, said patient has no symposysm, and after said administration for two months, the electrocardiogram of said patient became normal.

EXAMPLE 6

[Treatment of diabets]

The bioactive material of Example 1 was orally administered to a diabetic patient (male 62 years old, blood-sugar level about 400) in a dosage of 0.5g per day and a further 500cc of water in which pottery balls of Example 3 were dipped for 4 hours (5grs of pottery balls/1 l water) was orally administered per day. After said administration of said bioactive material and said water for 8 weeks, the blood-sugar level of said diabetic patient decreased to 95 and said blood-sugar level of said diabetic has maintained a normal range after said administration ceased.

EXAMPLE 7

[Treatment of cancer of the breast]

The bioactive material of Example 1 was orally administered to a patient (female 59 years old) suffering from cancer of the breast in its final stage, in a dosage of 1.0g per day and a further 600cc of water in which pottery balls of Example 3 were dipped for 5 hours (5grs of pottery balls/1l water) was orally administered per day. After said administration of said bioactive material and said water for 4 months, the tumors of the breast of said patient remarkably reduced, and then 0.5grs of said bioactive material and 600cc of said water per day were administered to said patient. Said treatment was continued for 5 months and substantially no tumors were recognized in her breast.

EXAMPLE 8

[Treatment of cancer of the rectum]

The bioactive material of Example 1 was orally administered to a patient (male 54 years old) suffering from cancer of the rectum which recurred two years after an operation, in a dosage of 1g per day and 2gs per day alternately. After said administration for 3 months, said patient recovered his health and, after said administration for 5 months, could return to work.

EXAMPLE 9

[Treatment of endometritis]

The bioactive material of Example 1 was orally administered to a patient (female 22 years old) suffering from serious endometritis in a dosage of 1g per day, and her endometritis was completely healed after said administration for 3 months.

EXAMPLE 10

[Treatment of menstrual disorders]

The bioactive material of Example 1 was orally administered to a patient (female 18 years old) suffering from menstrual disorders accompanied with serious menstrual colic, in a dosage of 0.2grs per day and her menstration became regular and said menstrual colic left her after said administration for 3 months.

EXAMPLE 11

[Treatment of dermatophytosis]

A powder mixture of 50% by weight of the bioactive material of Example 1 and 50% by weight of zinc flowers was applied on the affected parts of a patient (male 35 years old) suffering from dermatophytosis, once per day. Said treatment by said powder mixture was continued for a week and then said patient completely recovered from said dermatophytosis.

EXAMPLE 12

[Treatment of alopecia areata]

The bioactive material of Example 1 was orally administered to a patient (male 14 years old) suffering from alopecia areata, in a dosage of 0.5grs, twice (morning and evening) per day, and hair began to grow on his affected parts after said administration for one month.

EXAMPLE 13

[Treatment of otitis media]

The bioactive material of Example 1 was applied on the affected parts of a patient (female 34 years old) suffering from serious otitis media, twice per day (morning and evening), and said patient completely recovered from said otitis media after said treatment for one month.

EXAMPLE 14

[Treatment of pyorrhea alveolaris]

The bioactive material of Example 1 was applied on affected parts of a patient (female 55 years old) suffering from serious pyorrhea alveolaris, once per day, and no pus and bleeding from said patient's affected parts were recognized after said treatment for four weeks.

EXAMPLE 15

[Treatment of purpura]

The bioactive material of Example 1 was orally administered to a patient (female 46 years old) suffering from purpura for 6 years, in a dosage of 1g for per day and applied on her purple spots once a day, and her purple spots completely disappeared after said treatment for 3 months.

EXAMPLE 16

[Treatment of exophthalmic goiter]

The bioactive material of Example 1 was orally administered to a patient (female 46 years old) suffering from exophthalmic goiter for 6 years, in a dosage of 1.5grs per day and after said administration for 1 month, no swelling on said patient's throat was recognized.

EXAMPLE 17

[Preparation of an ointment]

As above described, the bioactive material of Example 1 is effective for treatment of cutaneous disorders. The bioactive material may be directly applied on affected parts, but the following recipes may also be recommended for ointments.

Lotion
Propylene glycol: 25gs
Triethanol amine: 1g
Water: 7gs
Oleic acid: 1.5gs
Polyethyleneglycolmonostearate: 11gs
Polyacrylic acid (2% by weight aq): 50gs
The bioactive material: 40gs
Cream
White oil: 41gs
Microcrystalline was: 3gs
Liquid lanolin: 10gs
Sorbitanmonooleate: 5gs
Polysorbate - 80: 0.25gs
Water: 41gs
The bioactive material: 35gs Said lotion and cream may be effective for the treatment or prevention of burns, wounds, dermatophytosis, freckles, spots, acne, haemorrhoids, and the like.

EXAMPLE 18

[Preparation of a tooth paste)

As above described, the bioactive material of Example 1 is effective for treatment of pyorrhea alveolaris. The bioactive material may be directly applied on an affected part, but the following recipe may also be recommended as a tooth paste.

Propylene glycol: 10gs
Water: 20gs
Polyethylene glycol monostearate: 2gs
Polyacrylic acid: 15gs
Calcium carbonate: 25gs
The bioactive material: 25gs
Clove oil: 0.1gs Said toothpaste may be effective for treatment or prevention of carious tooth, gingivitis, pyorrhea alveolaris, stomatitis, and the like.

EXAMPLE 19

[Preparation of a bioactive material]

A mixture of 50% by weight of pearl powder and 50% by weight of bone powder is heated at a temperature between 1,000° to 1,100° C. for 8 hours to obtain a bioactive material.

EXAMPLE 20

[Preservation of Flowers]

Rose were arranged in a vase in which water wherein the bioactive material of Example 19 was dispersed at a ratio of 1g/1l water. Flowers of said roses kept their fresh colour for 3 weeks while the colour of flowers faded for 3 days in a case where the roses were arranged in a vas containing untreated water.

EXAMPLE 21

[Manufacture of pottery balls]

A mixture of 50% by weight of pearl powder and 50% by weight of oyster shell powder was heated at a temperature between 700° to 800° C. for 7 hours and then about 20% by weight of said heat-treated mixture was mixed into potter's clay and said potter's clay was molded into balls having an average diameter of about 30mm. Said balls were heated at a temperature between 700° to 750° C. for 5 hours. Thus pottery balls having bioactivity were manufactured.

EXAMPLE 22

[Breeding of Carp]

Carp were bred in a tank in which 5t of water and 2kgs of balls of Example 21 were put in and said water kept clear for a long time without putrefaction and the good growth of said Carp without said Carp suffering from any disease was confirmed.

We claim:

1. Particle-form perarl heated to a temperature in the range 400°–1500° C. for a period of time in the range 5–30 hours.

2. An aqueous composition obtained by steeping in water particle form pearl in accordance with claim 1.

3. An ointment containing particle form pearl of claim 1.

4. A toothpaste containing particle form pearl in accordance with claim 1.

* * * * *

UNITED STATES PATENT AND TRADEMARK OFFICE
CERTIFICATE OF CORRECTION

PATENT NO. : 5,084,279
DATED : January 28, 1992
INVENTOR(S) : Masatoshi Kato and Masuhiro Kato It is certified that error appears in the above-identified patent and that said Letters Patent is hereby corrected as shown below:

Column 6, Claim 1, line 1, "perarl" should correctly read -- pearl --

Signed and Sealed this

Sixth Day of July, 1993

Attest:

MICHAEL K. KIRK

*Attesting Officer*  Acting Commissioner of Patents and Trademarks